United States Patent
Zhou et al.

(10) Patent No.: US 11,434,210 B2
(45) Date of Patent: Sep. 6, 2022

(54) METHOD FOR SYNTHESIZING VALSARTAN

(71) Applicant: Zhejiang Huahai Pharmaceutical Co., Ltd, Taizhou (CN)

(72) Inventors: Xiaohui Zhou, Taizhou (CN); Xiaoren Zhu, Taizhou (CN); Yuanxun Zhu, Taizhou (CN); Peng Dong, Taizhou (CN); Peng Wang, Taizhou (CN); Jinsheng Lin, Taizhou (CN); Wenquan Zhu, Taizhou (CN); Min Li, Taizhou (CN)

(73) Assignee: Zhejiang Huahai Pharmaceutical Co., Ltd, Taizhou (CN)

( * ) Notice: Subject to any disclaimer, the term of this patent is extended or adjusted under 35 U.S.C. 154(b) by 0 days.

(21) Appl. No.: 17/259,292

(22) PCT Filed: Jul. 17, 2018

(86) PCT No.: PCT/CN2018/096006
§ 371 (c)(1),
(2) Date: Jan. 11, 2021

(87) PCT Pub. No.: WO2020/010643
PCT Pub. Date: Jan. 16, 2020

(65) Prior Publication Data
US 2021/0269408 A1    Sep. 2, 2021

(30) Foreign Application Priority Data
Jul. 13, 2018 (CN) .......................... 201810771261.1

(51) Int. Cl.
*C07D 257/04* (2006.01)
(52) U.S. Cl.
CPC ................................. *C07D 257/04* (2013.01)
(58) Field of Classification Search
CPC .................................................. C07D 257/04
See application file for complete search history.

(56) References Cited

U.S. PATENT DOCUMENTS

2009/0203920 A1    8/2009   Welzig et al.

FOREIGN PATENT DOCUMENTS

| CN | 102010381 | 4/2011 |
| CN | 102863398 | 1/2013 |
| CN | 102911128 | 2/2013 |
| CN | 103012300 | 4/2013 |
| CN | 103613558 | 3/2014 |
| CN | 104045602 | 9/2014 |

OTHER PUBLICATIONS

Xu, Meng: "Research on the Synthesis of High Optical Purity Valsartan", Chinese Master's Theses Full-Textdatabase, Engineering Science & Technology I, No. 6, Jun. 15, 2012 (Jun. 15, 2012) (English Language Abstract, pp. 5-6).
State Intellectual Property Office of the P.R. China (ISA/CN), International Search Report for PCT/CN2018/096006, dated Sep. 7, 2018.

*Primary Examiner* — Shawquia Jackson
(74) *Attorney, Agent, or Firm* — Renner, Otto, Boisselle & Sklar, LLP

(57) ABSTRACT

A method for synthesizing valsartan, comprising the steps of: synthesizing a valsartan methyl ester intermediate to obtain a reaction mixture of the valsartan methyl ester intermediate; diluting the reaction mixture by salt water or water, and then using a first extraction solvent to extract the valsartan methyl ester intermediate; adding alkali to an organic layer containing the valsartan methyl ester intermediate for hydrolyzing, removing the organic layer, regulating pH of a water layer to be acidic by using acid, using the first extraction solvent to extract, concentrating a part of solvent, or distilling the solvent to dryness, and then adding a new solvent; finally, crystallizing, filtering, and drying to obtain the valsartan.

18 Claims, No Drawings

METHOD FOR SYNTHESIZING VALSARTAN

CROSS REFERENCE TO RELATED APPLICATIONS

This application is a national phase of International Application No. PCT/CN2018/096006 filed Jul. 17, 2018, and claims the priority of Chinese patent application No. 201810771261.1, with the title of "A METHOD FOR SYNTHESIZING HIGH PURITY VALSARTAN", filed on Jul. 13, 2018 before the China National Intellectual Property Administration, which are hereby incorporated by reference in their entirety.

FIELD OF THE INVENTION

The present application relates to the technical field of medicine, in particular to a method for synthesizing valsartan.

BACKGROUND OF THE INVENTION

Valsartan is a widely used clinical antihypertensive drug, which has the advantages of less side effects and good tolerance. Valsartan can also be used in the treatment of hypertension in patients with diabetes and nephropathy. The pharmacophore in valsartan molecule is biphenyltetrazole. In commercial production of valsartan, the most common construction strategy of the tetrazolium ring is to synthesize from cyanobiphenyl and azide at high temperature. The general commercial production route of valsartan is as follows:

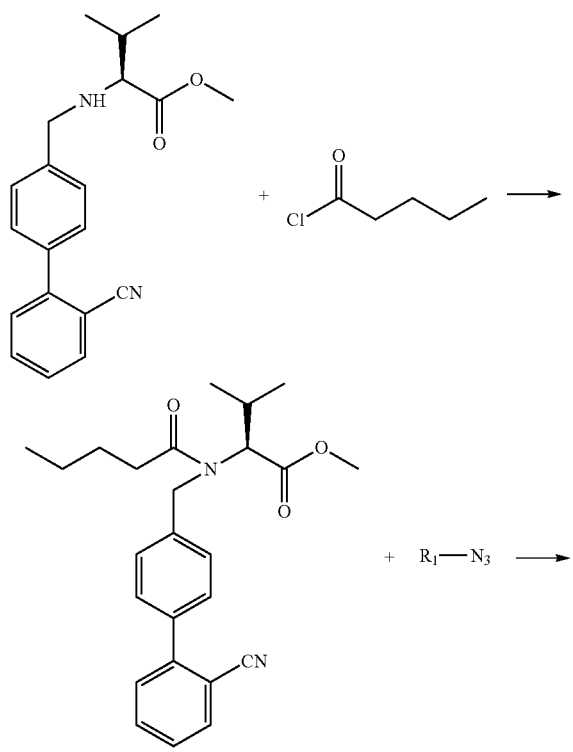

Valsartan cyanide intermediate

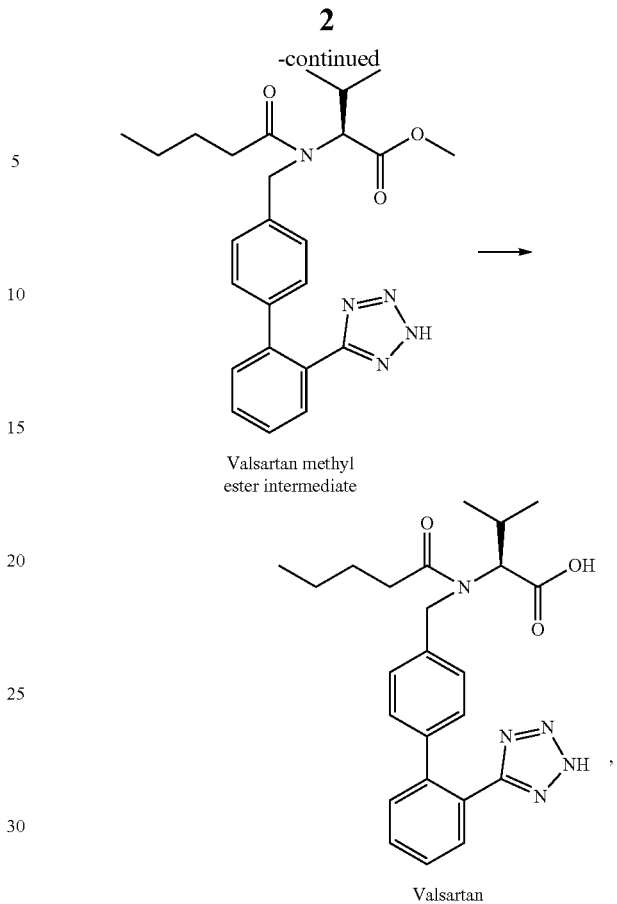

Valsartan methyl ester intermediate

Valsartan wherein $R_1$ represents a group such as Na, K or TMS.

In the above synthetic route of valsartan, the most suitable solvent in the process of tetrazolium cyclization is N,N-dimethylformamide (DMF). This is because DMF has excellent solubility and relatively high boiling point. In addition, when DMF is used as solvent, the conversion of valsartan cyanide is the highest, and the chiral molecules in valsartan cyanide are the most stable and are not prone to racemize and produce isomer impurities in DMF solvent at high temperature. Additionally, excessive azide, such as sodium azide, potassium azide or $TMSN_3$ is used in order to ensure the full conversion of valsartan cyanide intermediate in the reaction process in the commercial production. If the azide is not quenched after the reaction, toxic azide acid will be produced in the subsequent process. At the same time, when the material containing azide contacts with the material containing copper or other transition metal during the transfer process, it is prone to explode. Therefore, in order to ensure the safety of operation, the residual azide in the process must be quenched, and the method is to destroy the residual azide with nitrite under acidic conditions.

SUMMARY OF THE INVENTION

During the development of valsartan synthesis process, the inventors of the present application found that when DMF is used as solvent, DMF is prone to decompose and produce dimethylamine during high temperature reaction, and dimethylamine reacts with nitrite to produce highly toxic N-nitrosodimethylamine (NDMA) impurity during azide quenching treatment. If the valsartan methyl ester intermediate in valsartan process is not separated first, the resulting N-nitrosodimethylamine (NDMA) impurity will remain in valsartan API. The production route of NDMA is as follows:

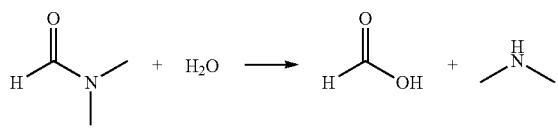

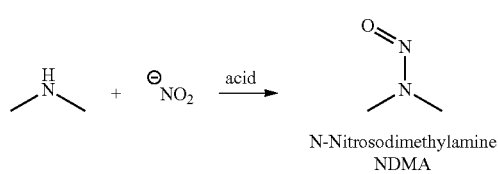

N-Nitrosodimethylamine
NDMA

In addition, patent reference CN103613558A also points out that in the process of quenching azide with nitrite under acidic conditions, a small amount of desvaleryl impurity in the valsartan methyl ester intermediate will react with nitrous acid to produce an N-nitroso compound, which will then be converted into valsartan impurity K in the subsequent process. The production process is as follows:

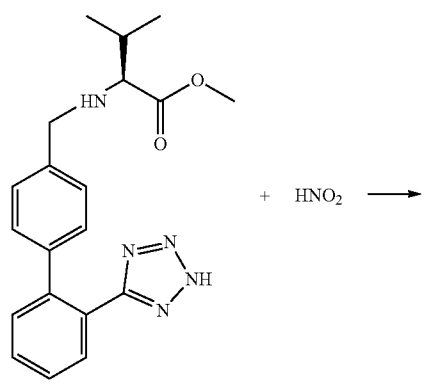

Valsartan methyl ester
desvaleryl impurity

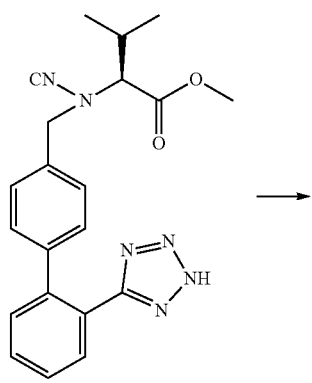

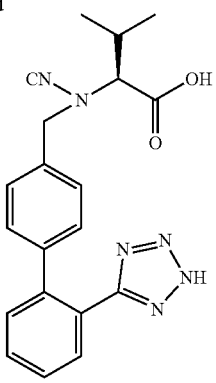

Valsartan impurity K

In patent reference CN103613558A, an improved strategy is to use sodium hypochlorite instead of sodium nitrite to quench azide. However, after further study, the inventors of the present application found that although the technical solution of CN103613558A can avoid the production of impurity K, it may also produce another highly toxic valsartan N-chloride impurity, of which the structural formula is as follows:

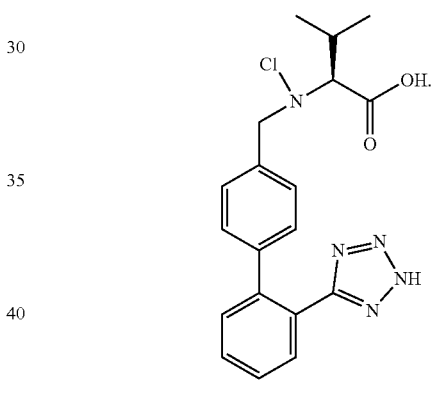

valsartan N-chloride

After further in-depth study of the synthetic process of valsartan, the inventor of the present application found that the possible introduction of highly toxic N-nitrosodimethylamine (NDMA), valsartan impurity K and valsartan N-chloride into valsartan API at the source of the process can be avoided by separating the valsartan methyl ester intermediate before azide was quenched. Further, a valsartan product with high purity (without the above impurities) is prepared by optimizing other operating conditions, such as controlling the water content in the solvent, crystallization temperature, and the like during crystallization. The present application is completed based on the above findings.

The purpose of the present application is to provide a method for synthesizing high purity valsartan, so that valsartan is synthesized without impurities, such as high toxic N-nitrosodimethylamine (NDMA), valsartan impurity K and valsartan N-chloride. The method comprises the following steps:

(1) synthesizing a valsartan methyl ester intermediate to obtain a reaction mixture containing the valsartan methyl ester intermediate;

In some specific embodiments of the present application, step (1) comprises: dissolving a valsartan cyanide intermediate in N,N-dimethylformamide (DMF), then adding azide and a first acid, heating and stirring to carry out tetrazolium cyclization reaction to synthesize the valsartan methyl ester intermediate, thereby obtaining a reaction mixture containing the valsartan methyl ester intermediate.

(2) diluting the reaction mixture with salt water or water, adding a first extraction solvent, and extracting the valsartan methyl ester intermediate after heating; after standing for layering, separating the water layer to obtain a first organic layer containing the valsartan methyl ester intermediate; washing the first organic layer at least once with salt water or water and separating the water layer to obtain a second organic layer containing the valsartan methyl ester intermediate;

In some specific embodiments of the present application, the water layer separated in step (2) can be combined, and the azide in the separated water layer can be quenched with a quenchant under acidic conditions.

(3) adding alkaline solution to the second organic layer containing the valsartan methyl ester intermediate; stirring for hydrolysis; after standing for layering, separating the organic layer, adjusting the pH of the water layer to acidity with a second acid, and then adding a second extraction solvent to the water layer to extract valsartan compounds; standing for layering to obtain a third organic layer containing valsartan compounds; controlling the water content in the third organic layer to be lower than a target value by adding a desiccant or removing water by distillation; adding a new solvent after the solvent in the third organic layer is partially concentrated or the solvent in the third organic layer is evaporated; crystallizing and filtering to obtain crude valsartan;

In some specific embodiments of the present application, the target value is a mass fraction of 2%, preferably 1%, more preferably 0.5%, and most preferably 0.35%.

(4) adding the valsartan crude product to a crystallization solvent, heating to dissolve, cooling, then holding for crystallizing, then filtering, washing the filter cake with the crystallization solvent and drying to obtain a finished valsartan product.

The structural formula of the valsartan mentioned in the present application is as follows:

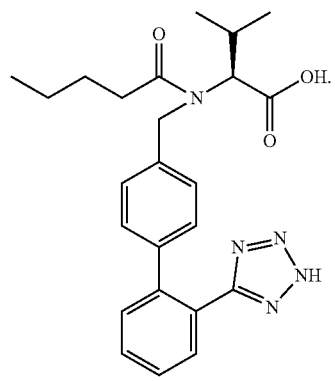

$C_{24}H_{29}N_5O_3$
Exact Mass: 435.227
Valsartan

The structural formula of the N-nitrosodimethylamine (N) mentioned in the present application is as follows:

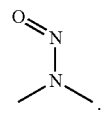

N-Nitrosodimethylamine
NDMA

The structural formula of the valsartan impurity K mentioned in the present application is as follows:

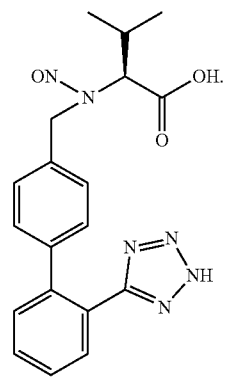

Valsartan impurity K

The structural formula of the valsartan N-chloride mentioned in the present application is as follows:

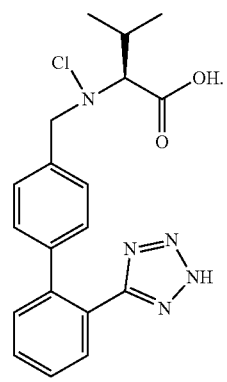

valsartan N-chloride

In the present application, the structural formula of the valsartan cyanide intermediate is as shown in Formula I.

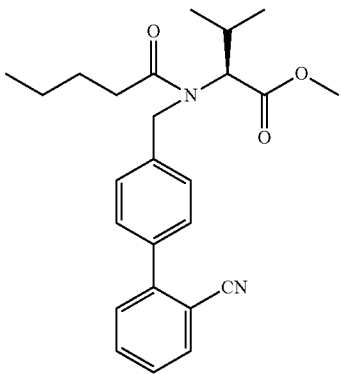

Formula I

In the present application, the structural formula of the valsartan methyl ester intermediate is shown in Formula II:

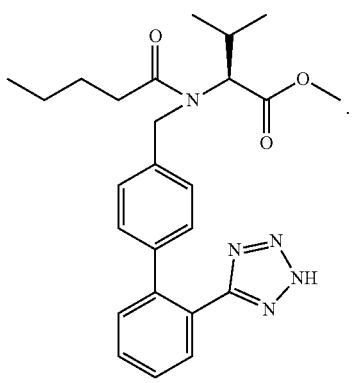

Formula II

In some specific embodiments of the present application, the azide in step (1) is selected from the group consisting of sodium azide, potassium azide, lithium azide, cesium azide, trimethylsilicon azide (TMSN$_3$), and the like or any combination thereof, preferably sodium azide, potassium azide or trimethylsilicon azide (TMSN$_3$).

In some specific embodiments of the present application, the first acid in step (1) is a Lewis acid; preferably; the first acid is selected from the group consisting of triethylamine hydrogen halide, triethylamine sulfate, triethylamine hydrogen sulfate, triethylamine phosphate, triethylamine hydrogen phosphate, trimethylamine hydrogen halide, trimethylamine sulfate, trimethylamine hydrogen sulfate, trimethylamine phosphate, trimethylamine hydrogen phosphate, diisopropyl ethylamine hydrogen halide, diisopropyl ethylamine sulfate, diisopropyl ethylamine hydrogen sulfate, diisopropyl ethylamine phosphate, pyridine hydrogen halide, pyridine sulfate, pyridine hydrogen sulfate, pyridine phosphate, pyridine hydrogen phosphate, N-methyl morpholine hydrogen halide, N-methyl morpholine sulfate, N-methyl morpholine hydrogen sulfate, N-methyl morpholine phosphate, N-methyl morpholine hydrogen phosphate, N-methyl piperidine hydrogen halide, N-methyl piperidine sulfate, N-methyl piperidine hydrogen sulfate, N-methyl piperidine phosphate, N-methyl piperidine hydrogen phosphate, N-methyl tetrahydropyrrole hydrogen halide, N-methyl tetrahydropyrrole sulfate, N-methyl tetrahydropyrrole hydrogen sulfate, N-methyl tetrahydropyrrole phosphate, N-methyl tetrahydropyrrole hydrogen phosphate, tributyltin chloride, anhydrous zinc chloride, zinc chloride dihydrate, anhydrous titanium tetrachloride, and the like; further preferably one of triethylamine hydrogen chloride, triethylamine sulfate, triethylamine hydrogen sulfate, pyridine hydrochloride and anhydrous zinc chloride or any combination thereof.

In the present application, the temperature of the tetrazole cyclization reaction in step (1) is 70-180° C., further preferably 100-140° C.

In some specific embodiments of the present application, the salt water in step (2) is selected from the group consisting of sodium chloride aqueous solution, magnesium chloride aqueous solution, potassium chloride aqueous solution, calcium chloride aqueous solution, and sodium sulfate aqueous solution or any combination thereof, further preferably saturated sodium chloride aqueous solution or sodium chloride aqueous solution with a mass fraction of 10-20%.

In some specific embodiments of the present application, the first extraction solvent in step (2) is a solvent capable of dissolving valsartan methyl ester intermediates and immiscible with water, preferably selected from the group consisting of toluene, xylene, dichloromethane, methyl tert-butyl ether, isopropyl ether, n-butyl ether, anisole, phenetole, n-hexyl ether and n-heptyl ether or any combination thereof, further preferably toluene, xylene, methyl tert-butyl ether, anisole or n-butyl ether.

In some specific embodiments of the present application, the heating temperature of heating extraction in step (2) is 35-140° C., preferably 45-100° C.

In some specific embodiments of the present application, the quenchant is selected from the group consisting of nitrite, hypochlorite and hypobromate or any combination thereof, preferably selected from the group consisting of sodium nitrite, potassium nitrite, sodium hypochlorite, sodium hypochlorite, calcium hypochlorite, and the like or any combination thereof, and preferably sodium nitrite or sodium hypochlorite.

In some specific embodiments of the present application, when the azide in the water layer is quenched, the acid used to form the acidic condition is an inorganic strong acid, preferably one of hydrochloric acid and sulfuric acid or any combination thereof; after adding acid, the pH value range is adjusted to 0-5, preferably 1-3.

In some specific embodiments of the present application, when the azide in the water layer is quenched in step (2), the temperature of the water layer is −5-40° C., preferably 5-20° C.

In some specific embodiments of the present application, the alkaline solution in step (3) is one of hydroxide: aqueous solution and carbonate aqueous solution or any combination thereof, further preferably 30% mass fraction of sodium hydroxide aqueous solution or 30% mass fraction of potassium hydroxide aqueous solution.

In some specific embodiments of the present application, the alkaline solution is added in step (3) and then the hydrolysis reaction is carried out by stirring. The hydrolysis reaction temperature is −10-40° C., preferably 0-20° C., and the reaction time is 5-40 hours, preferably 15-25 hours.

In some specific embodiments of the present application, in the step of adjusting the pH of the water layer to acidity with the second acid in step (3), the second acid used is an inorganic strong acid, preferably one of hydrochloric acid and sulfuric acid or any combination thereof. After adding acid, the pH value range is adjusted to 0.5-6, preferably 1-3.

In some specific embodiments of the present application, the second extraction solvent used in step (3) is a solvent that can be separated from the water layer, preferably ethyl acetate or methyl tert-butyl ether.

In some specific embodiments of the present application, the new solvent in step (3) is a single solvent or a mixture of a plurality of solvents capable of dissolving valsartan, preferably selected from the group consisting of ethyl acetate, acetone, ethanol, isopropanol and a mixed solvent of ethyl acetate and dichloromethane; more preferably, in the mixed solvent of ethyl acetate and dichloromethane, the volume ratio of ethyl acetate to dichloromethane is 1:3-3:1.

In some specific embodiments of the present application, the desiccant in step (3) is selected from the group consisting of anhydrous metal chloride salts, and anhydrous metal sulfate or combination thereof, preferably anhydrous magnesium sulfate or anhydrous sodium sulfate.

In some specific embodiments of the present application, the crystallization solvent described in step (4) is a single solvent or a mixed solvent of a plurality of solvents capable of dissolving valsartan, preferably ethyl acetate or a mixed solvent of ethyl acetate and dichloromethane; more preferably, in the mixed solvent of ethyl acetate and dichloromethane, the volume ratio of ethyl acetate to dichloromethane is 1:3-3:1.

The method for synthesizing valsartan provided in the present application ensures the safety of valsartan by separating the valsartan methyl ester intermediate before quenching the azide, and avoiding the possible introduction of impurities, such as the highly toxic N-nitrosodimethylamine (NDMA), valsartan impurity K and valsartan N-chloride produced during the azide quenching process into the valsartan methyl ester intermediate and further into the valsartan API.

DETAILED DESCRIPTION OF THE INVENTION

In order to make the purpose, technical solution and advantages of the present invention more clear, the following examples are listed to further explain the present invention in detail. It is apparent that the examples described herein are only some examples of the present invention but not all examples. All other examples obtained by those skilled in the art without creative efforts fall within the protection scope of the present invention based on the examples of the present invention.

Example of Synthesis of Valsartan

In the following examples and comparative examples of the present application, the GC-MS method is used to detect N-nitrosodimethylamine (NDMA) in the finished product of valsartan, and the LC-MS method is used to detect the valsartan impurities K and valsartan N-chloride in the finished product of valsartan. First of all, the GC-MS (gas chromatography-mass spectrometry) and LC-MS (liquid chromatography-mass spectrometry) testing methods used in examples and comparative examples of the present application are described as follows.

1. Chromatographic conditions and detection methods of GC-MS:

Instrument: ThermoFischer gas chromatography single quadrupole mass spectrometry (Trace 1300 & ISQLT)

Chromatographic column: DB-1701, 60 m×0.32 min, 1.8 μm (14% cyariopropylphenyl—86% dimethylpolysiloxane copolymer)

Carrier gas: helium
Linear velocity: 1.0 mL/min
Inlet temperature: 180° C.
Injection volume: 2.0 μL
Split ratio: 25:1
Heating procedure:
The initial temperature is 60° C., holding for 2 min, then heating up to 240° C. at a rate of 15° C./min, and holding for 5 min.
Ion source mode: EI, positive ion
Ion source: 250° C.
Temperature of Quadrupole: 160° C.
Relative voltage: 200V
Scanning mode: single ion extraction mode (SIM)
SIM ion current: m/z 74.1)
Diluent: DMSO
Blank solution: the same as the diluent;

Preparation of standard solution for reference substance of N-nitrosodimethylamine (NDMA): an appropriate amount of reference substance of N-nitrosodimethylamine (NDMA) was diluted with the diluent to a concentration of 0.2, 0.8, 3.2, 6.4, and 20 μg/mL of NDMA, respectively, shaking to completely dissolve before use.

Determination of the amount of N-nitrosodimethylamine (NDMA) in the samples to be detected (the finished products of valsartan prepared in the following examples and comparative examples):

400 mg of the sample to be detected was accurately weighed into a 20 mL headspace bottle. 2 mL diluent was then accurately added, shaken to dissolve and mixed well as the test solution. The above GC-MS method was used to detect the test solution and NDMA standard solution of different concentrations. The standard curve method was used to calculate the NDMA amount in the sample to be detected.

2. Chromatographic conditions and detection methods of LC-MS:

Instrument: Agilent LC-QTOF high precision liquid chromatography-mass spectrometry (Agilent 6120 & 6545)

Chromatographic column: Waters Symmetry C8, 250×4.6 mm; 5 μm
Mobile phase A: 0.1% formic acid aqueous solution
Mobile phase B: acetonitrile
Column temperature: 35° C.
Injection volume: 10 μL
Detection wavelength: 230 nm (DAD spectrum 200-400 nm full scan)
Gradient table:

| Time (min) | Mobile phase A (% V/V) | Mobile phase B (% V/V) | Flow rate (mL/min) |
| --- | --- | --- | --- |
| 0 | 50 | 50 | 1.2 |
| 4 | 50 | 50 | 1.2 |
| 16 | 20 | 80 | 1.2 |
| 14 | 20 | 80 | 1.2 |
| 26 | 50 | 50 | 1.2 |
| 35 | 50 | 50 | 1.2 |

Ion source: ESI ion source
Mass spectrometer detector parameters:

| Mass spectrometry detector parameters | | | |
| --- | --- | --- | --- |
| Dry gas flow rate | 6 L/min | $MS_1$ scan mode | Full scan |
| Dry gas temperature | 325° C. | $MS_1$ scan time | 5-40 min |

-continued

| Mass spectrometry detector parameters | | | |
|---|---|---|---|
| Gas-atomized pressure | 35 psi | $MS_1$ scan range | m/z 100-1700 |
| Capillary voltage | +3500 V | Sheath air flow rate | 12 L/min |
| Ion mode | ESI positive ion | Sheath gas temperature | 350° C. |
| Fragment voltage | 90 V | Target ion 1 | m/z 381.167 (valsartan impurity K) |
| Target ion 2 | m/z 386.138 (valsartan N-chloride) | Ion extraction error | 10 ppm |

Preparation of standard solution for reference substance of valsartan impurity K: are appropriate amount of reference substance of valsartan impurity K was diluted with the diluent (0.1% formic acid aqueous solution:acetonitrile=2:11 (v/v)) to a concentration of 0.2, 0.8, 3.2, 6.4, 20 μg/mL, respectively; shaking to completely dissolve before use.

Preparation of standard solution for reference substance of valsartan N-chloride: an appropriate amount of reference substance of valsartan N-chloride was diluted with the diluent (0.1% formic acid aqueous solution:acetonitrile=2:1 (v/v)) to a concentration of 0.2, 0.8, 3.2, 6.4, 20 μg/mL, respectively, shaking to completely dissolve before use.

Detection of the amount of valsartan impurity K in the sample to be detected: 400 mg of the sample to be detected was accurately weighed into a 20 mL headspace bottle, then 2 mL diluent (0.1% formic acid aqueous solution:acetonitrile=2:1) was accurately added, which was shaken to dissolve and mixed well as the test solution. The above GC-MS method was used to detect the test solution and valsartan impurity K standard solutions of different concentrations. The standard curve method was used to calculate the amount of valsartan impurity K in the sample to be detected.

Detection of the amount of valsartan N-chloride in the sample to be detected: 400 mg of the sample to be detected was accurately weighed into a 20 mL headspace bottle, then 2 mL diluent (0.1% formic acid aqueous solution:acetonitrile=2:1) was accurately added, which was shaken to dissolve and mixed well as the test solution. The above GC-MS method was used to detect the test solution and valsartan N-chloride standard solutions of different concentrations. The standard curve method was used to calculate the valsartan N-chloride amount in the sample to be detected.

EXAMPLE 1

Synthesis of Valsartan 100 mL of valsartan cyanide intermediate in N,N-dimethylformamide (DNIT) (containing 70 g of valsartan cyanide intermediate) was added into a reaction bottle, and then 36 g of anhydrous zinc chloride and 25 g of sodium azide were added, heating to 125-135° C. and stirring for 28 hours. After the reaction was over, the temperature was lowered to 45-48° C., and then 500 mL of methyl tert-butyl ether and 400 mL of 20% (w/w) sodium chloride aqueous solution were added, stirring at 45-48° C. for 1 hour. After stirring was over, the reaction solution was allowed to stand for layering, and the water layer was separated. 200 mL of saturated salt water was added into the organic layer at 45-48° C., which was washed and stirred for 2 hours and the water layer was separated. The organic layer was further washed and stirred with 200 mL of saturated salt water at the same temperature for 2.5 hours. The organic layer was separated. The 3 portions of the separated water layer was combined and used in the subsequent azide quenching process.

The finally separated organic layer was transferred into another reaction bottle, and cooled to 10-15° C. 55 mL of 30% (w/w) NaOH aqueous solution and 105 of water were then added, which was stirred for 15-20 hours and then allowed to stand for layering. The methyl tert-butyl ether layer was separated. The temperature of the water layer was further lowered to 0-10° C. 4 mol/L hydrochloric acid solution was dropwise added until the pH is 1-2. 600 mL of ethyl acetate was then added, which was stirred for 30 minutes, and the water layer was separated. 350 mL of ethyl acetate was then evaporated under reduced pressure at 40° C. if the water content was higher than 0.4%, 200 mL of fresh ethyl acetate was added (the water amount was less than 0.01% (w/w)), and then 200 mL of ethyl acetate was evaporated at 40° C. until the water content was less than or equal to 0.4% (w/w) (the final water content was 0.35% (w/w)). The resultant was cooled to 0-10° C., crystallized for 10 hours and filtered to obtain a valsartan crude product, which was directly introduced into the crystallization process of valsartan finished product without drying.

The valsartan crude product obtained in the previous step was put into a reaction bottle, and then 400 mL of ethyl acetate was added. The reaction was heated to 35-40° C., stirred to dissolve and clarify, and then slowly cooled to 10-20° C., and crystallized for 2 hours. After stirring was over, the resultant was filtered, and the filter cake was washed with 30 mL of ethyl acetate at 10-15° C. and dried to obtain 63 g of a valsartan finished product, yield 85%.

N-nitrosodimethylamine (NDMA) in the valsartan finished product was detected by GC-MS method. Valsartan impurity K and valsartan N-chlorides in the valsartan finished product were detected by LC-MS method. The results were undetected (the impurity concentration was lower than the detection limit of the detection method, no peak).

Quenching of Azide

The previously combined water layer was transferred into a reaction bottle, and 13 g of sodium nitrite was added. The temperature was lowered to 15° C. 90 mL of 3 mol/L dilute hydrochloric acid solution was then slowly added. The reaction was stirred for 30 minutes to quench the azide. After further concentration and desalination, the wastewater can be discharged into a low concentration wastewater pool for further treatment.

EXAMPLE 2

Synthesis of Valsartan 100 mL of valsartan cyanide intermediate in N,N-dimethylformamide (DMF) (containing 60 g of valsartan cyanide intermediate) was added into a reaction bottle, and then 34 g of anhydrous zinc chloride and 29 g of potassium azide were added. The reaction was heated to 135-140° C. and stirred for 20 hours. After the reaction was over, the temperature was lowered to 90-100° C. 600 mL of n-butyl ether and 460 mL of 20% (w/w) sodium chloride aqueous solution were then added, which was stirred at 90-100° C. for 3 hours. After stirring was over, the reaction solution was allowed to stand for layering, and the water layer was separated. 200 mL of saturated salt water was added into the organic layer at 90-100° C., which was washed and stirred for 2 hours, and the water layer was separated. The organic layer was further washed and stirred with 200 mL of saturated salt water at the same temperature for 2 hours, and the organic layer was separated. The 3 portions of the separated Water layer was combined and used in the subsequent azide quenching process.

The finally separated organic layer was transferred into another reaction bottle, and cooled to 10-15° C. 50 mL of 30% (w/w) NaOH aqueous solution and 100 mL of water were then added, which was stirred for 15-20 hours and then allowed to stand for layering. The n-butyl ether layer was separated. The temperature of the water layer was further lowered to 0-10° C. 4 mol/L sulfuric acid solution was dropwise added so that the pH was 1-3. 550 mL of ethyl acetate was then added, which was stirred for 30 minutes, and the water layer was separated. 50 g of anhydrous magnesium sulfate was then added, which was stirred for 2 hours until the water content was 0.2%. The resultant was filtered, and magnesium sulfate was removed. 340 mL of ethyl acetate was then evaporated at 40° C. The resultant was cooled to 0-5° C., crystallized for 8 hours and filtered to obtain a valsartan crude product, which was directly introduced into the crystallization process of valsartan finished product without drying.

The valsartan crude product obtained in the previous step was put into a reaction bottle, and then 300 mL of ethyl acetate was added. The reaction was heated to 40-42° C., stirred to dissolve and clarify, and then slowly cooled to 0-5° C., and further crystallized for 2 hours. After stirring was over, the resultant was filtered, and the filter cake was washed with 30 mL of ethyl acetate at 0-2° C. and dried to obtain 55.3 g of a valsartan finished product, yield 86%.

N-nitrosodimethylamine (NDMA) in the valsartan finished product was detected by GC-MS method. Valsartan impurity K and valsartan N-chlorides in the valsartan finished product were detected by LC-MS method. The results were undetected.

Quenching of Azide

The previously combined water layer was transferred to a reaction bottle, and 12 g of sodium hypochlorite was added. The temperature was adjusted to 15° C. 120 mL of 2 mol/L dilute hydrochloric acid solution was then slowly added. The reaction was stirred for 30 minutes to quench the azide. After further concentration and desalination, the wastewater can be discharged into a low concentration wastewater pool for further treatment.

EXAMPLE 3

Synthesis of Valsartan 130 mL of valsartan cyanide intermediate in N,N-dimethylformamide (DMF) (containing 80 g of valsartan cyanide intermediate) was added into a reaction bottle, and then 45 g of anhydrous zinc chloride and 30 g of sodium azide were added. The reaction was heated to 130-135° C. and stirred for 24 hours. After the reaction was over, the temperature was lowered to 90-100° C. 440 mL of toluene and 440 mL of 20% (w/w) sodium chloride aqueous solution were then added, which was stirred at 90-100° C. for 2 hours. After stirring was over, the reaction solution was allowed to stand for layering, and the water layer was separated. 220 mL of saturated salt water was added into the organic layer at 90-100° C., which was washed and stirred for 2 hours, and the water layer was separated. The organic layer was further washed and stirred with 220 mL of saturated salt water at the same temperature for 2 hours, and the organic layer was separated. The 3 portions of separated water layer was combined and used in the subsequent azide quenching process.

The finally separated organic layer was transferred into another reaction bottle, cooled to 10-15° C., and then 65 mL of 30% NaOH aqueous solution and 140 mL of water were added. The reaction was stirred for 15-20 hours and then allowed to stand for layering. The toluene layer was separated. The temperature of the water layer was further lowered to 0-10° C. 6 mol/L hydrochloric acid solution was dropwise added so that the pH was 1-2, and then 700 mL of ethyl acetate was added. The reaction was stirred for 30 minutes, and the water layer was separated. 400 mL of ethyl acetate was then evaporated under reduced pressure at 40° C. If the water content was higher than 0.5%, 200 mL of fresh ethyl acetate was added (the water content was less than 0.01%), and then 200 mL of ethyl acetate was evaporated at 40° C. until the water content was less than or equal to 0.5% (the final water content was 0.28%). The resultant was cooled to 0-10° C., crystallized for 10 hours and filtered to obtain a valsartan crude product, which was directly put into the crystallization process of valsartan finished product without drying.

The valsartan crude product obtained in the previous step was put into a reaction bottle, and then 540 mL of ethyl acetate was added. The reaction was heated to 40-45° C., stirred to dissolve and clarify, and then slowly cooled to −5-5° C., and crystallized for 2 hours. After stirring was over, the resultant was filtered, and the filter cake was then washed with 50 mL of ethyl acetate at 0-2° C. and dried to obtain 75.6 g of a valsartan finished product, yield 87%.

N-nitrosodimethylamine (NDMA) in the valsartan finished product was detected by GC-MS method. Valsartan impurity K and valsartan N-chlorides in the valsartan finished products were detected by LC-MS method. The results were undetected.

Quenching of Azide

The previously combined water layer was transferred to a reaction bottle, and 15 g of sodium nitrite was added. The temperature was lowered to 10° C. 120 mL of 3 mol/L dilute hydrochloric acid solution was then slowly added. The reaction was stirred for 30 minutes to quench the azide. After further concentration and desalination, the wastewater can be discharged into a low concentration wastewater pool for further treatment.

EXAMPLE 4

Synthesis of Valsartan 250 mL of valsartan cyanide intermediate in N,N-dimethylformamide (DMF) (containing 160 g of valsartan cyanide intermediate) was added into a reaction bottle, and then 92 g of anhydrous zinc chloride and 106 g of trimethylsilyl azide (TMSN$_3$) were added. The reaction was heated to 130-135° C. and stirred for 28 hours. After reaction was over, the temperature was lowered to 90-100° C. 800 mL of toluene and 850 mL of 20% (w/w) sodium chloride aqueous solution were then added. The reaction was stirred at 90-100° C. for 2 hours. After stirring was stopped, the reaction solution was allowed to stand for layering, and the water layer was separated. 450 mL of saturated salt water was added into the organic layer at 90-100° C., which was washed and stirred for 3 hours, and the water layer was separated. The organic layer was further washed and stirred with 450 mL of saturated salt water at the same temperature for 3 hours. The organic layer was separated. The 3 portions of the separated water layer was combined and used in the subsequent azide quenching process.

The finally separated organic layer was transferred into another reaction bottle, cooled to 10-15° C., and then 130 mL of 30% (w/w) NaOH aqueous solution and 280 mL of water were added. The reaction was stirred for 14-18 hours, and then allowed to stand for layering. The xylene layer was separated. The temperature of the water layer was further lowered to −5-10° C., 6 mol/L hydrochloric acid solution was dropwise added so that the pH was 1.0-2.0. 1500 mL of ethyl acetate was then added. The reaction was stirred for 30 minutes, and the water layer was separated. 900 mL of ethyl acetate was then evaporated under reduced pressure at 40° C. If the water content was higher than 0.3%, 200 mL of fresh ethyl acetate was added (the water content was less than 0.01%), and then 200 mL of ethyl acetate was evaporated at 40° C. until the water content was less than to 0.3% (the final water content was 0.25%). The resultant was cooled to −5-10° C., crystallized for 12 hours and filtered to obtain a valsartan crude product, which was directly put into the crystallization process of valsartan finished product without drying.

The valsartan crude product obtained in the previous step was put into a reaction bottle, and then 1000 mL of ethyl acetate was added. The reaction was heated up to 40-45° C., stirred to dissolve and clarify, and then slowly cooled to 0-3° C., and crystallized for 3 hours. After stirring was over, the resultant was filtered, and the filter cake was then washed with 80 mL of ethyl acetate at 0-2° C. and dried to obtain 150.8 g of a valsartan finished product, yield 88%.

N-nitrosodimethylamine (NDMA) in the valsartan finished product was detected by GC-MS method. Valsartan impurity K and valsartan N-chlorides in the valsartan finished product were detected by LC-MS method. The results were undetected.

Quenching of Azide

The previously combined water layer was transferred to a reaction bottle, and 30 g of sodium nitrite was added. The temperature was lowered to 15° C. 200 mL of 3 mol/L dilute sulfuric acid solution was then slowly added. The reaction was stirred for 30 minutes to quench the azide. After further concentration and desalination, the wastewater can be discharged into a low concentration wastewater pool for further treatment.

EXAMPLE 5

Synthesis of Valsartan 130 mL of valsartan cyanide intermediate in N,N-dimethylformamide (DMF) (containing 80 g of valsartan cyanide intermediate) was added into a reaction bottle, and then 48 g of triethylamine hydrochloride and 30 g of sodium azide were added. The reaction was heated to 120-125° C. and stirred for 28 hours. After reaction was over, the temperature was lowered to 90-100° C. 450 mL of toluene and 200 mL of water were then added. The reaction was stirred at 90° C. for 2 hours. After stirring was over, the reaction solution was allowed to stand for layering, and the water layer was separated. 260 mL of saturated salt water was added into the organic layer at 90-100° C., which was washed and stirred for 2 hours, and the water layer was separated. The organic layer was further washed and stirred with 260 mL of saturated salt water at the same temperature for 2 hours. The organic layer was separated. The 3 portions of the separated water layer was combined and used in the subsequent azide quenching process.

The finally separated organic layer was transferred to another reaction bottle, and cooled to 5-10° C. 65 mL 30% NaOH aqueous solution and 140 mL water were then added. The reaction was stirred for 20-25 hours. The toluene layer was separated. The temperature of water layer was lowered to 0-10° C. 6 mol/L hydrochloric acid solution was dropwise added so that the pH was 1-3. 700 mL ethyl acetate was then added. The reaction was stirred for 30 minutes, and the water layer was separated. 400 mL ethyl acetate was then evaporated at 40° C., under reduced pressure. If the water content is higher than 0.5%, 200 mL of fresh ethyl acetate was added (water content is less than 0.01%), and then 200 mL ethyl acetate was evaporated at 40° C. under reduced pressure until the water content is less than or equal to 0.5% (the final water content is 0.25%). The resultant was cooled to 0-10° C., crystallized for 10 hours, and filtered to obtain a crude valsartan product, which was introduced into the crystallization process of valsartan finished product directly without drying.

The valsartan crude product obtained n the previous step was put into a reaction bottle, and then 700 mL of mixture of ethyl acetate—dichloromethane (volume ratio is 2:1) was added. The reaction was heated to 40-45° C., stirred to dissolve and clarify, then slowly cooled to −5-5° C., and crystallized for 2 hours. After stirring was over, the resultant was filtered, then the filter cake was washed with 50 mL of ethyl acetate at 0-2° C. and dried to obtain 69.4 g of a valsartan finished product, yield 81%.

N-nitrosodimethylamine (NDMA) in the valsartan finished product was detected by GC-MS method. Valsartan impurity K and valsartan N-chlorides in the valsartan finished product were detected by LC-MS method. The results were undetected.

Quenching of Azide

The previously combined water layer was transferred to a reaction bottle, and 20 g of potassium nitrite was added. The temperature was lowered to 10° C. 120 mL of 3 mol/L dilute hydrochloric acid solution was then slowly dropwise added. The reaction was stirred for 30 minutes to quench the azide. After further concentration and desalination, the wastewater can be discharged into a low concentration wastewater pool for further treatment.

EXAMPLE 6

Synthesis of Valsartan 130 mL of valsartan cyanide intermediate in N,N-dimethylformamide (DMF) (containing 80 g of valsartan cyanide intermediate) was added into a reaction bottle, and then 42 g of triethylamine sulfate and 50 g of trimethylsilyl azide (TMSN$_3$) were added. The reaction was heated to 110-120° C. and stirred for 35 hours. After the reaction was over, the temperature was lowered to 90-100° C. 500 mL of toluene and 500 mL of 20% sodium chloride aqueous solution were then added. The reaction was stirred at 90° C. for 2 hours. After stirring was over, the reaction solution was allowed to stand for layering, and the water layer was separated. 250 mL of saturated salt water was added into the organic layer at 90-100° C., which was washed and stirred for 2 hours, and the water layer was separated. The organic layer was further washed and stirred with 250 mL of saturated salt water at the same temperature for 2 hours, and the organic layer was separated. The 3 portions of the separated water layer was combined and used in the subsequent azide quenching process.

The finally separated organic layer was transferred into another reaction bottle, cooled to 5-15° C., and then 60 mL of 30% NaOH aqueous solution and 120 mL of water were added. The reaction was stirred for 20-25 hours, and then allowed to stand for layering. The toluene layer was separated. The temperature of the water layer was further lowered to 0-10° C. 6 mol/L hydrochloric acid solution was dropwise added so that the pH was 2-3, and then 700 mL of ethyl acetate was added. The reaction was stirred for 30 minutes, and the water layer was separated. 80 g of anhydrous sodium sulfate was then added. The reaction was stirred for 2 hours until the water content was 0.18%. The resultant was filtered, and sodium sulfate was removed. 400 mL of ethyl acetate was then evaporated at 40° C. under reduced pressure. The resultant was cooled to 0-5° C., crystallized for 8 hours and filtered to obtain a valsartan crude product, which was directly introduced into the crystallization process of valsartan finished products without drying.

The valsartan crude product obtained in the previous step was put into a reaction bottle, and then 1000 mL of mixture of ethyl acetate—dichloromethane (volume ratio is 1:1) was added. The reaction was heated to 40-45° C., stirred to dissolved and clarify, then slowly cooled to −5-5° C., and crystallized fiver 2 hours. After stirring was over, the resultant was filtered, then the filter cake was washed with 100 mL of mixture of ethyl acetate—dichloromethane (volume ratio 1:1) at 0-2° C. and dried to obtain 62.6 g of a valsartan finished product, yield 73%.

N-nitrosodimethylamine (NDMA) in the valsartan finished product was detected by GC-MS method. Valsartan impurity K and valsartan N-chlorides in the valsartan finished product were detected by LC-MS method. The results were undetected.

Quenching of Azide

The previously combined water layer was transferred to a reaction bottle, and 13 g of calcium hypochlorite was added. The temperature was lowered to 10° C. 100 mL of 3 mol/L dilute sulfuric acid solution was then slowly dropwise added. The reaction was stirred for 30 minutes to quench the azide. After further concentration and desalination, the wastewater can be discharged into a low concentration wastewater pool for further treatment.

EXAMPLE 7

Synthesis of Valsartan 250 mL of valsartan cyanide intermediate in N,N-dimethylformamide (DMF) (containing 160 g of valsartan cyanide intermediate) was added into a reaction bottle, and then 130 g of triethylamine hydrosulfate and 106 g of trimethylsilyl azide ($IMSN_3$) were added. The reaction was heated to 130-135° C. and stirred for 28 hours. After the reaction was over, the temperature was lowered to 75-85° C. 800 mL of anisole and 500 mL of 10% sodium chloride aqueous solution were then added. The reaction was stirred at 75-85° C. for 2 hours. After stirring was over, the reaction solution was allowed to stand for layering, and the water layer was separated. 450 mL of saturated salt water was added into the organic layer at 75-85° C., which was washed and stirred for 3 hours, and the water layer was separated. The organic layer was further washed and stirred with 450 mL of saturated salt water at the same temperature for 3 hours, and the organic layer was separated. The e portions of the separated water layer was combined and used in the subsequent azide quenching process.

The finally separated organic layer was transferred into another reaction bottle, cooled to 10-15° C., and then 130 mL of 30% NaOH aqueous solution and 280 mL of water were added. The reaction was stirred for 15-18 hours, and then allowed to stand for layering. The anisole layer was separated. The temperature of the water layer was further lowered to −5-0° C. 6 mol/L hydrochloric acid solution was dropwise added so that the pH was 1.5-2.5, and then 1500 mL of ethyl acetate was added. The reaction was stirred for 30 minutes, and the water layer was separated. All ethyl acetate was then evaporated under reduced pressure at 40° C., and then 600 mL of acetone was added. The reaction was heated to 40° C. until completely dissolved. The final water content was 0.17%. The temperature was slowly cooled to 0-5° C. The resultant was crystallized for 12 hours and filtered to obtain a valsartan crude product, which was directly introduced into the crystallization process of valsartan finished product without drying.

The valsartan crude product obtained in the previous step was put into a reaction bottle, and then 1000 mL of ethyl acetate was added. The reaction was heated to 40-45° C., stirred to dissolved and clarify, then slowly cooled to 0-3° C., and crystallized for 3 hours. After stirring was over, the resultant was filtered, then the filter cake was washed with 80 mL of ethyl acetate at 0-2° C. and dried to obtain 140.6 g of a valsartan finished product, yield 82%.

N-nitrosodimethylamine (NDMA) in the valsartan finished product was detected by GC-MS method. Valsartan impurity K and valsartan N-chlorides in the valsartan finished product were detected by LC-MS method. The results were undetected.

Quenching of Azide

The previously combined water layer was transferred to a reaction bottle, and 30 g of sodium nitrite was added. The temperature was lowered to 15° C. 180 mL of 3 mol/L dilute hydrochloric acid solution was then slowly dropwise added. The reaction was stirred for 30 minutes to quench the azide. After further concentration and desalination, the wastewater can be discharged into a low concentration wastewater pool for further treatment.

EXAMPLE 8

Synthesis of Valsartan 130 mL of valsartan cyanide intermediate in N,N-dimethylformamide (DMF) (containing 80 g of valsartan cyanide intermediate) was added into a reaction bottle, and then 95 g of pyridine hydrochloride and 30 g of sodium azide were added. The reaction was heated to 130-140° C. and stirred for 24 hours. After the reaction was over, the temperature was lowered to 90-100° C. 440 mL of toluene and 440 mL of 20% magnesium chloride aqueous solution were then added. The reaction was stirred at 90° C. for 2 hours. After stirring was over, the reaction solution was allowed to stand for layering, and the water layer was separated. 300 mL of saturated magnesium chloride aqueous solution was added into the organic layer at 90-100° C., which was washed and stirred for 2 hours, and the water layer was separated. The organic layer was further washed and stirred with 300 mL of saturated magnesium chloride aqueous solution at the same temperature for 2 hours, and the organic layer was separated. The 3 portions of the separated water layer was combined and used in the subsequent azide quenching process.

The finally separated organic layer was transferred into another reaction bottle, and cooled to 10-15° C. 65 mL of 30% NaOH aqueous solution and 140 mL of water were then added. The reaction was stirred for 15-20 hours, and then allowed to stand for layering. The toluene layer was separated. The temperature of the water layer was further lowered to 0-10° C. 6 mol/L hydrochloric acid solution was dropwise added so that the pH is 2-3, and then 700 mL of ethyl acetate was added. The reaction was stirred for 30 minutes, and the water layer was separated. All ethyl acetate was then evaporated under reduced pressure at 40° C., and then 500 mL of isopropanol was added. The reaction was heated to 40° C. until completely dissolved. The final water content was 0.15%. The temperature was lowered to 0-10° C. The resultant was crystallized for 10 hours and filtered to obtain a valsartan crude product, which was directly introduced into the crystallization process of valsartan finished product without drying.

The valsartan crude product obtained in the previous step was put into a reaction bottle, and then 540 mL of ethyl acetate was added. The reaction was heated up to 40-45° C., stirred to dissolved and clarify, then slowly cooled to −5-5° C., and crystallized for 2 hours. After stirring was over, the resultant was filtered, then the filter cake was washed with 50 mL of ethyl acetate at 0-2° C. and dried to obtain 80.0 g of a valsartan finished product, yield 84%.

N-nitrosodimethylamine (NDMA) in the valsartan finished product was detected by GC-MS method. Valsartan impurity K and valsartan N-chlorides in the valsartan finished product were detected by LC-MS method. The results were undetected.

Quenching of Azide

The previously combined water layer was transferred to a reaction bottle, and 35 g of sodium hypobromite was added. The temperature was lowered to 10° C. 120 mL of 3 mol/L dilute hydrochloric acid solution was then slowly dropwise added. The reaction was stirred for 30 minutes to quench the azide. After further concentration and desalination, the wastewater can be discharged into a low concentration wastewater pool for further treatment.

EXAMPLE 9

Synthesis of Valsartan 100 mL of valsartan cyanide intermediate in N,N-dimethylformamide (DMF) (containing 60 g of valsartan cyanide intermediate) was added into a reaction bottle, and then 34 g of anhydrous zinc chloride and 25 g of sodium azide were added. The reaction was heated to 130-135° C. and stirred for 28 hours. After the reaction was over, the temperature was lowered to 60-70° C. 1000 mL of anisole and 460 mL of 20% sodium sulfate aqueous solution were then added. The reaction was stirred at 60-70° C. for 3 hours. After stirring was over, the reaction solution was allowed to stand for layering, and the water layer was separated. 200 mL of saturated sodium sulfate aqueous solution was added into the organic layer at 60-70° C., which was washed and stirred for 2 hours, and the water layer was separated. The organic layer was further washed and stirred with 200 mL of saturated sodium sulfate aqueous solution at the same temperature for 2 hours, and the organic layer was separated. The 3 portions of the separated water layer was combined and used in the subsequent azide quenching process.

The finally separated organic layer was transferred into another reaction bottle, and cooled to 5-15° C. 60 mL of 30% NaOH aqueous solution and 100 mL of water were then added. The reaction was stirred for 15-20 hours, and then allowed to stand for layering. The anisole layer was separated. The temperature of the water layer was further lowered to 0-10° C. 6 mol/L hydrochloric acid solution was dropwise added so that the pH was 1-3, and then 550 mL of ethyl acetate was added. The reaction was stirred for 30 minutes, and the water layer was separated. 50 g of anhydrous magnesium sulfate was then added. The resultant was stirred for 2 hours until the water content was 0.21%. The resultant was filtered, and magnesium sulfate was removed. 340 mL of ethyl acetate was then evaporated at 40° C., cooled to 0-5° C., crystallized for 8 hours and filtered to obtain a valsartan crude product, which was directly introduced into the crystallization process of valsartan finished products without drying.

The valsartan crude product obtained in the previous step was put into a reaction bottle, and then 300 mL of ethyl acetate was added. The reaction was heated to 40-42° C., stirred to dissolved and clarify then slowly cooled to 0-5° C., and crystallized for 2 hours. After stirring was over, the resultant was filtered, then the filter cake was washed with 30 mL of ethyl acetate at 0-2° C. and dried to obtain 57.2 g of a valsartan finished product, yield 89%.

N-nitrosodimethylamine (NDMA) in the valsartan finished product was detected by GC-MS method. Valsartan impurity K and valsartan N-chlorides in the valsartan finished product were detected by LC-MS method. The results were undetected.

Quenching of Azide

The previously combined water layer was transferred to the reaction bottle, and 12 g of sodium hypochlorite was added. The temperature was adjusted to 15° C. 120 mL of 2 mol/L dilute hydrochloric acid solution was then slowly dropwise added, and stirred for 30 minutes to quench the azide. After further concentration and desalination, the wastewater can be discharged into a low concentration wastewater pool for further treatment.

EXAMPLE 10

Synthesis of Valsartan 130 mL of valsartan cyanide intermediate in N,N-dimethylformamide (DMF) (containing 80 g of valsartan cyanide intermediate) was added into a reaction bottle, and then 45 g of anhydrous zinc chloride and 30 g of sodium azide were added. The reaction was heated to 130-140° C. and stirred for 24 hours. After the reaction was over, the temperature was lowered to 80-90° C., and then 500 mL of xylene and 440 mL of 20% sodium chloride aqueous solution were added. The reaction was stirred for 2 hour at 80-90° C. After stirring was over, the reaction solution was allowed to stand for layering, and the water layer was separated. 220 mL of saturated salt water was added into the organic layer at 80-90° C., which was washed and stirred for 2 hours, and the water layer was separated. The organic layer was further washed and stirred with 220 mL of saturated salt water at the same temperature for 2 hours. The organic layer was separated. The 3 portions of the separated water layer was combined and used in the subsequent azide quenching process.

The finally separated organic layer was transferred into another reaction bottle, and cooled to 10-15° C. 65 mL of 30% NaOH aqueous solution and 140 mL of water were then added. The reaction was stirred for 15-20 hours, and then allowed to stand for layering. The xylene layer was separated. The temperature of the water layer was further lowered to 0-10° C., 6 mol/L hydrochloric acid solution was dropwise added so that the pH was 1-2, and then 700 mL of ethyl acetate was added. The reaction was stirred for 30 minutes, and the water layer was separated. 400 mL of ethyl acetate was then evaporated under reduced pressure at 40°

C. if the water content was higher than 0.5%, 200 mL of fresh ethyl acetate was added (the water content was less than 0.01%), and then 200 mL of ethyl acetate was evaporated at 40° C. until the water content was 0.24%. The resultant was cooled to 5-8° C., crystallized for 10 hours and filtered to obtain a valsartan crude product, which was directly introduced into the crystallization process of valsartan finished product without drying.

The valsartan crude product obtained in the previous step was put into a reaction bottle, and then 900 mL of mixture of ethyl acetate—dichloromethane (volume ratio is 1:3) was added. The reaction was heated to 40-45° C., stirred to dissolved and clarify, then slowly cooled to 5-10° C., and crystallized for 2 hours. After stirring was over, the resultant was filtered, then the filter cake was washed with 90 mL of mixture of ethyl acetate—dichloromethane (volume ratio 1:3) at 5-8° C. and dried to obtain 71.1 g of a valsartan finished product, yield 83%.

N-nitrosodimethylamine (NDMA) in the valsartan finished product was detected by GC-MS method. Valsartan impurity K and valsartan N-chlorides in the valsartan finished product were detected by LC-MS method. The results were undetected.

Quenching of Azide

The previously combined water layer was transferred to the reaction bottle, and 35 g of calcium hypobromite was added. The temperature was lowered to 10° C. 120 mL of 3 mol/L dilute hydrochloric acid solution was then slowly added. The reaction was stirred for 30 minutes to quench the azide. After further concentration and desalination, the wastewater can be discharged into a low concentration wastewater pool for further treatment.

EXAMPLE 11

Synthesis of Valsartan 130 mL of valsartan cyanide intermediate in N,N-dimethylformamide (DMF) (containing 80 g of valsartan cyanide intermediate) was added into a reaction bottle, and then 45 g of anhydrous zinc chloride and 30 g of sodium azide were added. The reaction was heated to 130-140° C. and stirred for 24 hours. After the reaction was over, the temperature was lowered to 60-70° C., and then 600 mL of n-butyl ether and 440 mL of 20% sodium chloride aqueous solution were added. The reaction was stirred at 60-70° C. for 3 hours. After stirring was over, the reaction solution was allowed to stand for layering, and the water layer was separated. 220 mL of saturated salt water was added into the organic layer at 60-70° C., which was washed and stirred for 2 hours, and the water layer was separated. The organic layer was further washed and stirred with 220 mL of saturated salt water at the same temperature for 2 hours, and the organic layer was separated. The 3 portions of separated water layer was combined and used in the subsequent azide quenching process.

The finally separated organic layer was transferred into another reaction bottle, and cooled to 5-15° C. 90 mL of 30% KOH aqueous solution and 150 mL of water were then added. The reaction was stirred for 18-23 hours, and then allowed to stand for layering. The n-butyl ether layer was separated. The temperature of the water layer was further lowered to 0-10° C. 6 mol/L hydrochloric acid solution was dropwise added so that the pH was 2-3, and then 700 mL of ethyl acetate was added. The reaction was stirred for 30 minutes, and the water layer was separated. 50 g of anhydrous magnesium sulfate was then added. The resultant was stirred for 2 hours until the water content was 0.2%. The resultant was filtered, and magnesium sulfate was removed. 340 mL of ethyl acetate was then evaporated at 40° C. The resultant was cooled to 0-10° C., crystallized for 10 hours and filtered to obtain a valsartan crude product, which was directly introduced into the crystallization process of valsartan finished product without drying.

The valsartan crude product obtained in the previous step was put into a reaction bottle, and then 540 mL of ethyl acetate was added. The reaction was heated to 40-45° C., stirred to dissolved and clarify, then slowly cooled to −5-5° C., and crystallized for 2 hours. After stirring was over, the resultant was filtered, then the filter cake was washed with 50 mL of ethyl acetate at 0-2° C. and dried to obtain 65.1 g of a valsartan finished product, yield 76%.

N-nitrosodimethylamine (NDMA) in the valsartan finished product was detected by GC-MS method. Valsartan impurity K and valsartan N-chlorides in the valsartan finished product were detected by LC-MS method. The results were undetected.

Quenching of Azide

The previously combined water layer was transferred to the reaction bottle, and 15 g of sodium nitrite was added. The temperature was lowered to 10° C. 120 mL of 3 mol/L dilute hydrochloric acid solution was then slowly dropwise added. The reaction was stirred for 30 minutes to quench the azide. After further concentration and desalination, the wastewater can be discharged into a low concentration wastewater pool for further treatment.

EXAMPLE 12

Synthesis of Valsartan 130 mL of valsartan cyanide intermediate in N,N-dimethylformamide (DMF) (containing 80 g of valsartan cyanide intermediate) was added into a reaction bottle, and then 45 g of anhydrous zinc chloride and 30 g of sodium azide were added. The reaction was heated to 130-135° C. and stirred for 22 hours. After the reaction was over, the temperature was lowered to 75-80° C., and then 500 mL of toluene and 400 mL of 20% sodium chloride aqueous solution were added. The reaction was stirred at 75-80° C. for 2 hours. After stirring was over, the reaction solution was allowed to stand for layering, and the water layer was separated. 200 mL of saturated salt water was added into the organic layer at 75-80° C., which was washed and stirred for 2 hours, and the water layer was separated. The organic layer was further washed and stirred with 200 mL of saturated salt water at the same temperature for 2 hours, and the organic layer was separated. The 3 portions of the separated water layer was combined and used in the subsequent azide quenching process.

The finally separated organic layer was transferred into another reaction bottle, and cooled to 1.0-15° C. 65 mL of 30% NaOH aqueous solution and 140 mL of water were then added. The reaction was stirred for 15-20 hours, and then allowed to stand for layering. The toluene layer was separated. The temperature of the water layer was further lowered to 0-10° C. 6 mol/L hydrochloric acid solution was dropwise added so that the pH was 1-2, and then 700 mL of ethyl acetate was added. The reaction was stirred for 30 minutes, and the water layer was separated. All ethyl acetate was then evaporated under reduced pressure at 40° C., and then 400 mL of isopropanol was added, which was heated to 40° C. until clear (the final water content was 0.21%). The temperature was lowered to 0-10° C. The resultant was crystallized for 10 hours and filtered to obtain a valsartan crude product, which was directly introduced into the crystallization process of valsartan finished product without drying.

The valsartan crude product obtained in the previous step was put into the reaction bottle, and then 540 mL of ethyl acetate was added. The reaction was heated to 40-45° C., stirred to dissolved and clarify, then slowly cooled to −5-5° C., and crystallized for 2 hours. After stirring was over, the resultant was filtered, then the filter cake was washed with 50 mL of ethyl acetate at 0-2° C., and dried to obtain 70.3 g of a valsartan finished product, yield 82%.

N-nitrosodimethylamine (NDMA) in the valsartan finished product was detected by GC-MS method. Valsartan impurity K and valsartan N-chlorides in the valsartan finished product were detected by LC-MS method. The results were undetected.

Quenching of Azide

The previously combined water layer was transferred to a reaction bottle, and 15 g of sodium nitrite was added. The temperature was lowered to 10° C. 120 mL of 3 mol/L dilute hydrochloric acid solution was then slowly added. The reaction was stirred for 30 minutes to quench the azide. After further concentration and desalination, the wastewater can be discharged into a low concentration wastewater pool for further treatment.

COMPARATIVE EXAMPLE 1

130 mL of valsartan cyanide intermediate in N,N-dimethylformamide (DMF) was added to a reaction bottle (containing 80 g of valsartan cyanide intermediate). 45 g of anhydrous zinc chloride and 30 g of sodium azide were then added. The reaction was heated to 130-135° C. and stirred for 24 hours. After the reaction was over, the temperature was lowered to 30-50° C. 50 mL of DMF, 3000 mL of methyl tert-butyl ether and 200 mL of water were then added. The reaction was stirred at 30-50° C. for 1 hour, and cooled to 0-10° C. 12 g of sodium nitrite was then added. The resultant was stirred for 30 min. 110 mL of 6 mol/L dilute hydrochloric acid solution were slowly dropwise added at 0-10° C. with stirring so that the pH value was 1-2. The resultant was allowed to stand for layering, and the organic layer was separated.

The separated organic layer was transferred to another reaction bottle, and cooled to 10-15° C. 65 mL 30% NaOH aqueous solution and 140 mL water were then added. The reaction was stirred for 15-20 hours, and then allowed to stand for layering. The toluene layer was separated. The water layer was further cooled to 0-10° C. 6 mol/L hydrochloric acid solution was added so that the pH value was 1-2, and then 700 mL ethyl acetate was added. The reaction was stirred for 30 minutes, and the water layer was separated. 400 mL ethyl acetate was then evaporated under vacuum at 40° C. If the water content is higher than 0.5%, 200 mL of fresh ethyl acetate was further added (water content is less than 0.01%), and then 200 mL ethyl acetate was evaporated at 40° C. under reduced pressure until the water content is less than or equal to 0.5% (the final water content was 0.28%). The resultant was cooled to 0-10° C., crystallized for 15 hours, and filtered to obtain a crude valsartan product, which was directly introduced into the crystallization process of valsartan finished product without drying.

The obtained valsartan crude product was put into a reaction bottle, and then 540 mL of ethyl acetate was added. The reaction was heated to 40-45° C., stirred to dissolve and clarify, then slowly cooled to −5-5° C., and crystallized for 2 hours. After stirring was over, the resultant was filtered, then the filter cake was washed with 50 mL of ethyl acetate at 0-2° C. and dried to obtain 73.7 g of the finished products of valsartan, yield 86%.

N-nitrosodimethylamine (NDMA) in valsartan finished product was detected by GC-MS method. Valsartan impurities K and valsartan N-chlorides in valsartan finished product were detected by LC-MS method. The contents of impurities were calculated by standard curve method. The results showed that the content of N-nitrosodimethylamine (NDMA) was 22.6 ppm, and the content of valsartan impurities K was 47.5 ppm. The content of valsartan N-chlorides was not detected.

COMPARATIVE EXAMPLE 2

100 of valsartan cyanide intermediate in N,N-dimethylformamide (DMF) was added to a reaction bottle (containing 60 g of valsartan cyanide inter mediate). 34 g of anhydrous zinc chloride and 25 g of sodium azide were then added. The reaction was heated to 130-135° C. and stirred for 28 hours. After the reaction was over, the temperature was lowered to 30-50° C. 40 mL of DMF, 2400 mL of methyl tert-butyl ether and 150 mL of water were then added. The reaction was stirred at 30-50° C. for 1 hour, and cooled to 0-10° C. 16 g of sodium hypochlorite was then added. The resultant was stirred for 30 min. 100 mL of 6 mol/L dilute sulfuric acid solution were slowly dropwise added at 0-10° C. with stirring so that the pH was 1-2. The resultant was allowed to stand for layering, and the organic layer was separated.

The separated organic layer was transferred into another reaction bottle, and cooled to 5-10° C. 60 mL of 30% NaOH aqueous solution and 100 mL of water were then added. The reaction was stirred for 10-20 hours, and then allowed to stand for layering. The anisole layer was removed. The temperature of the water layer was further lowered to 0-10° C. 6 mol/L hydrochloric acid solution was dropwise added so that the pH was 1-3, and then 550 mL of ethyl acetate was added. The resultant was stirred for 30 minutes, and the water layer was separated. 50 g of anhydrous magnesium sulfate was then added. The resultant was stirred for 2 hours until the water content was 0.21%, and filtered to remove magnesium sulfate. 340 mL of ethyl acetate was then evaporated at 40° C. under reduced pressure, cooled to 0-5° C., crystallized for 8 hours and filtered to obtain the valsartan crude product, which was directly introduced into the crystallization process of finished products of valsartan without drying.

The obtained valsartan crude product was put into the reaction bottle, and then 300 mL of ethyl acetate was added. The reaction was heated to 40-42° C., stirred to dissolved and clarify, then slowly cooled to 0-5° C., and crystallized for 2 hours. After stirring was aver, the resultant was filtered, then the filter cake was washed with 30 mL of ethyl acetate at 0-2° C. and dried to obtain 56.6 g of the finished products of valsartan, yield 88%.

N-nitrosodimethylamine (NDMA) in valsartan finished product was detected by GC-MS method. Valsartan impurities K and valsartan N-chlorides in valsartan finished product were detected by LC-MS method. The contents of impurities were calculated by standard curve method. The results showed that the content of N-nitrosodimethylamine (NDMA) and the content of valsartan impurities K were not detected. The content of valsartan N-chlorides was 28.3 ppm.

The above only provides a detailed description of the preferred embodiments of the present invention. The present invention is not limited to the above embodiments, and any alternation and variation of the present invention belong to the protection scope of the present invention.

The invention claimed is:

1. A method for synthesizing valsartan, wherein the valsartan prepared does not comprise N-nitrosodimethylamine, valsartan impurity K and valsartan N-chloride; wherein the method comprises the following steps:
   (1) synthesizing a valsartan methyl ester intermediate to obtain a reaction mixture containing the valsartan methyl ester intermediate;
   wherein the step (1) comprises: dissolving a valsartan cyanide intermediate in N,N-dimethylformamide, then adding azide and a first acid, heating and stirring to carry out tetrazolium cyclization reaction to synthesize the valsartan methyl ester intermediate, thereby obtaining a reaction mixture containing the valsartan methyl ester intermediate;
   (2) diluting the reaction mixture with salt water or water, adding a first extraction solvent, and heating extraction the valsartan methyl ester intermediate; obtaining a first organic layer containing the valsartan methyl ester intermediate by standing for layering and separating the water layer; washing the first organic layer at least once with salt water or water and separating the water layer to obtain a second organic layer containing the valsartan methyl ester intermediate;
   (3) adding an alkaline solution to the second organic layer containing the valsartan methyl ester intermediate, stirring to hydrolysis, standing for layering; after separating the organic layer, adjusting the pH of the water layer to acidity with a second acid, and then adding a second extraction solvent to the water layer to extract valsartan compounds; standing for layering to obtain a third organic layer containing valsartan compounds; controlling the water content in the third organic layer to be lower than a target value by adding a desiccant or removing water by distillation; adding a new solvent when the solvent in the third organic layer is partially concentrated or the solvent in the third organic layer is evaporated, crystallizing and filtering to obtain a valsartan crude product; and
   (4) adding the valsartan crude product to a crystallization solvent, heating to dissolve, cooling, crystallizing, and filtering, then washing the filter cake with the crystallization solvent and drying to obtain a finished valsartan product;
   wherein the target value in step (3) is a mass fraction of 2%;
   wherein the structures of the valsartan cyanide intermediate and the valsartan methyl ester intermediate are shown in the following Formula I and Formula II, respectively:

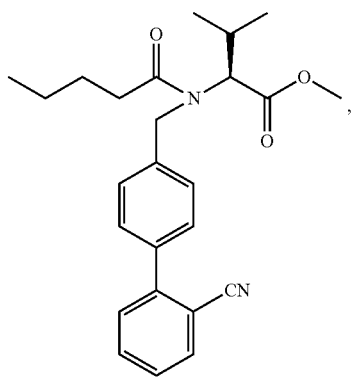

Formula I

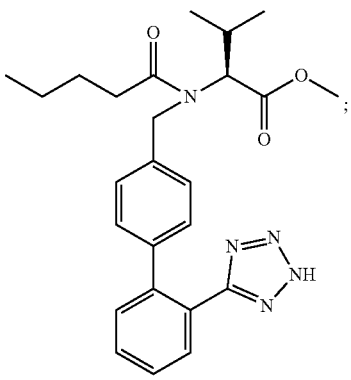

Formula II wherein the structure of the valsartan impurity K is as follows:

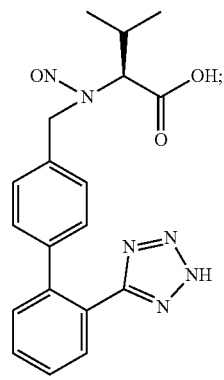

valsartan impurity K and the structure of the valsartan N-chloride is as follows:

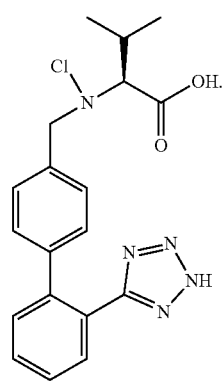

valsartan N-chloride

2. The method according to claim 1, wherein the azide described in step (1) is selected from the group consisting of sodium azide, potassium azide, lithium azide, cesium azide and trimethylsilicon azide or any combination thereof.

3. The method according to claim 1, wherein the first acid in step (1) is a Lewis acid.

4. The method according to claim 1, wherein the temperature of the tetrazole cyclization reaction in step (1) is 70-180° C.

5. The method according to claim 1, wherein the salt water in step (2) is selected from the group consisting of one of sodium chloride aqueous solution, magnesium chloride aqueous solution, potassium chloride aqueous solution, calcium chloride aqueous solution, and sodium sulfate aqueous solution or any combination thereof.

6. The method according to claim 1, wherein the first extraction solvent in step (2) is an organic solvent capable of dissolving valsartan methyl ester intermediates and immiscible with water.

7. The method according to claim 1, wherein the temperature of heating extraction in step (2) is 35-140° C.

8. The method according to claim 1, wherein the water layer separated in step (2) is combined, and the azide in the separated water layer can be quenched with a quenchant under acidic conditions, wherein the quenchant is selected from the group consisting of nitrite, hypochlorite and hypobromate or any combination thereof.

9. The method according to claim 1, wherein, when the azide in the water layer is quenched, the acid used to form the acidic condition is an inorganic strong acid; after adding acid, the pH value range is 0-5.

10. The method according to claim 1, wherein the alkaline solution in step (3) is one of hydroxide aqueous solution and carbonate aqueous solution or any combination thereof.

11. The method according to claim 1, wherein the alkaline solution is added and then the hydrolysis reaction is carried out with stirring in step (3), wherein the hydrolysis reaction temperature is −10-40° C.

12. The method according to claim 1, wherein in the step of adjusting the pH of the water layer to acidity with the second acid in step (3), the second add used is an inorganic strong acid.

13. The method according to claim 1, wherein the second extraction solvent used in step (3) is a solvent that can be separated from the water layer.

14. The method according to claim 1, wherein the new solvent in step (3) is a single solvent or a mixture of multiple solvents capable of dissolving valsartan.

15. The method according to claim 1, wherein the desiccant in step (3) is selected from the group consisting of anhydrous metal chloride salts; and anhydrous metal sulfate or combination thereof.

16. The method according to claim 1, wherein the crystallization solvent in step (4) is a single solvent or a mixture of multiple solvents capable of dissolving valsartan.

17. The method according to claim 1, wherein the azide in step (1) is selected from the group consisting of sodium azide, potassium azide and trimethylsilicon azide.

18. The method according to claim 1, wherein the first acid in step (1) is selected from the group consisting of triethylamine hydrogen halide, triethylamine sulfate, triethylamine hydrogen sulfate, triethylamine phosphate, triethylamine hydrogen phosphate, trimethylamine hydrogen halide, trimethylamine sulfate, trimethylamine hydrogen sulfate, trimethylamine phosphate, trimethylamine hydrogen phosphate, diisopropyl ethylamine hydrogen halide, diisopropyl ethylamine sulfate, diisopropyl ethylamine hydrogen sulfate, diisopropyl ethylamine phosphate, pyridine hydrogen halide, pyridine sulfate, pyridine hydrogen sulfate, pyridine phosphate, pyridine hydrogen phosphate, N-methyl morpholine hydrogen halide, N-methyl morpholine sulfate, N-methyl morpholine hydrogen sulfate, N-methyl morpholine phosphate, N-methyl morpholine hydrogen phosphate, N-methyl piperidine hydrogen halide, N-methyl piperidine sulfate, N-methyl piperidine hydrogen sulfate, N-methyl piperidine phosphate, N-methyl piperidine hydrogen phosphate, N-methyl tetrahydropyrrole hydrogen halide, N-methyl tetrahydropyrrole sulfate, N-methyl tetrahydropyrrole hydrogen sulfate, N-methyl tetrahydropyrrole phosphate, N-methyl tetrahydropyrrole hydrogen phosphate, tributyltin chloride, anhydrous zinc chloride, zinc chloride dihydrate, and anhydrous titanium tetrachloride, or any combination thereof.

* * * * *